United States Patent
Mossman et al.

(10) Patent No.: US 6,239,321 B1
(45) Date of Patent: May 29, 2001

(54) UPGRADING LIGHT OLIGOMERS

(75) Inventors: Allen B. Mossman, Wheaton; Egils Vitands, Lisle, both of IL (US)

(73) Assignee: BP Amoco Corporation, Chicago, IL (US)

( * ) Notice: Subject to any disclaimer, the term of this patent is extended or adjusted under 35 U.S.C. 154(b) by 0 days.

(21) Appl. No.: 09/513,953

(22) Filed: Feb. 28, 2000

(51) Int. Cl.⁷ .......................... C07C 2/04; C10M 105/04
(52) U.S. Cl. ................ 585/10; 585/12; 585/16; 585/510; 585/515; 508/591
(58) Field of Search .............. 585/10, 510–516, 585/16, 17, 18

(56) References Cited

U.S. PATENT DOCUMENTS

| | | | |
|---|---|---|---|
| 3,903,001 | * 9/1975 | Gates et al. | 252/78 |
| 4,078,010 | * 3/1978 | Prillieux et al. | 252/73 |
| 4,301,315 | * 11/1981 | Haskell et al. | 585/304 |
| 4,356,339 | * 10/1982 | Imaizumi et al. | 585/829 |
| 5,180,865 | * 1/1993 | Heilman et al. | 585/10 |
| 5,436,379 | * 7/1995 | Heilman et al. | 585/10 |
| 5,475,147 | * 12/1995 | Zak | 568/569 |

* cited by examiner

Primary Examiner—Ellen M. McAvoy
(74) Attorney, Agent, or Firm—James R. Henes

(57) ABSTRACT

A process for upgrading a feedstock comprising lower oligomers and higher oligomers of isobutylene by oligomerizing the lower oligomer fraction thereof to higher molecular weight components.

20 Claims, 3 Drawing Sheets

UPGRADING LIGHT OLIGOMERS

BACKGROUND OF THE INVENTION

1. Field of the Invention

The present invention relates to a process for upgrading a mixture of oligomers of isobutylene or of a mixture of isobutylene and a minor amount of n-butenes and to the composition of the upgraded oligomers and their use as traction fluids.

2. Discussion of the Prior Art

Streams comprising monomers and oligomers of isobutylene or of a mixture of isobutylene and a minor amount of n-butenes are available from a variety of sources. For example, the manufacture of polyisobutylene from streams comprising isobutylene or of a mixture of isobutylene and a minor amount of n-butenes also results in the production of a large volume of a mixture of oligomers of isobutylene and, if present, n-butenes that have a lower molecular weight than the polyisobutylene produced. This mixture is sometimes referred to as light polymer gasoline and typically is made up primarily of unreacted monomers and dimers, trimers and tetramers of isobutylene and, if present, n-butenes. Such mixtures are commonly used as an inexpensive feedstock in, for example, a refinery. It would be highly desirable to convert components of these mixtures to higher oligomers that are suitable for use in other more valuable applications.

Numerous methods have been reported for converting dimers and trimers of butenes to higher oligomers of butenes. For example, each of E. C. Erdolchemie Gmbh, German Patent No. DE 3611842 and E. C. Petrochemical Gmbh, German Patent No. DE 3612443 A1 discloses a process in which diisobutylene is dimerized in the liquid phase in the presence of a sulphonated cation exchange resin catalyst. The resin is pre-dried at 120–200° C., and the diisobutylene is pretreated with a dried inorganic adsorbent. By means of a partial return of the generated reaction product, it is possible to obtain nearly complete conversion of diisobutylene to tetraisobutylene. In one example, the yield for the conversion of diisobutylene to tetraisobutylene was 95%. There was no disclosure that other oligomers besides tetraisobutylene were formed.

Other references disclose processes that differ in significant ways from the process of the present invention but which produce products that are similar in oligomeric distribution but which products differ from the compositions of the present invention. For example, International Patent Application No. PCT/FI92/00199, published as WO 93/02993 on Feb. 18, 1993, discloses a method for the oligomerization of 1-butene in a single step in the presence of a catalytic complex of $BF_3$ and either water, a $C_2$–$C_{10}$ monoalcohol or a $C_2$–$C_8$ monocarboxylic acid as the cocatalyst. Several specific examples of the oligomerization afforded high selectivities for the production of tetramers and pentamers, as follows:

| | $C_4$ Conversion | Selectivities for the Production of $C_4$ Conversion | | | | | |
|---|---|---|---|---|---|---|---|
| | Conversion | $C_8$ | $C_{12}$ | $C_{16}$ | $C_{20}$ | $C_{24}$ | $C_{28}$ | $C_{32+}$ |
| Example 1 | 77.4% | — | 10.5 | 51.5 | 28.2 | 8.0 | 1.8 | — |
| Example 9 | 53.5% | 0.3 | 7.6 | 43.3 | 36.8 | 7.1 | 5.0 | — |

In addition, Example 15 afforded combined selectivities of 57.0% for dimers, trimers and tetramers and of 43.0% for pentamers, hexamers and heptamers.

International Patent Application No. PCT/FI93/00540, published as WO94/15895 on Jul. 21, 1994, discloses a method for the oligomerization of olefins containing 6 to 20 carbon atoms or n-butenes in the presence of a catalytic complex of $BF_3$ and either water, a $C_2$–$C_{10}$ monoalcohol or a C2–C10 monocarboxylic acid as the cocatalyst. Several specific examples of the oligomerization afforded high selectivities for the production of tetramers and pentamers, as follows:

| | Selectivities for the Production of | | |
|---|---|---|---|
| | $C_8$–$C_{16}$ | $C_{20}$–$C_{28}$ | $C_{32+}$ |
| Example 19 | 58.3 | 39.2 | 2.5 |
| Example 25 | 59.6 | 34.5 | 5.9 |
| Example 54 | 63.2 | 35.6 | — |

The olefin oligomerized was an n-butene mixture in Example 19, and n-butene in Example 25. In addition, Example 9 in International Patent Application No. PCT/FI93/00540 was a duplicate of Example 15 in aforesaid International Patent Application No. PCT/FI92/00199.

Japanese Patent No. 57-159724 published on Mar. 27, 1981 and issued on Oct. 1, 1982 discloses a method for the selective conversion of a dimer of isobutylene to a tetramer of isobutylene in the presence of an aluminosilicate, acid gypsum or activated gypsum catalyst that must be roasted prior to use. The patent illustrates that when equimolar amounts of dimers and trimers of isobutylene are present in the feedstock for the reaction, the method was essentially ineffective. When the molar amounts of the dimers to trimers of isobutylene in the feedstock were in a ratio of 9:1, the method was effective.

Thus far, no one has disclosed a method for converting the aforesaid light oligomers of isobutylene and optionally n-butenes to mixtures of higher oligomers thereof, in which mixtures of tetramers, pentamers, hexamers and higher oligomers are the major components and have the overall oligomeric distribution and iosmeric structure of the composition of this invention.

In addition, it would be highly desirable to develop improved traction fluids. Continuously variable transmissions are expected to be the next generation technology in automotive power transmission. Continuously variable transmissions transmit power through a traction drive mechanism. Traction drive power transmissions, which transmit power to a driven part through a traction device mechanism, have attracted attention in the field of automobiles and industrial machinery, and in recent years research and development thereon has progressed. The traction drive mechanism is a power transmitting mechanism using a rolling friction. Unlike conventional drive mechanisms it does not use any gears, which enables a reduction in vibration and noise as well as a smooth speed change in high-speed rotation.

An important goal in the automobile industry is improvement in the fuel economy of automobiles. It has been suggested that if the traction drive is applied to the transmission of automobiles to convert the transmission to a continuous variable-speed transmission the fuel consumption can be reduced compared to conventional transmission systems since the drive can always be in the optimum speed ratio.

Traction fluid is a term used to identify a class of lubricants that give improved performance in traction drive. More particularly, a traction fluid is used in a device, such as a non-stage transmission device for automobiles, in which traction drive transfers force from one rotating rigid body to another through rolling contact. The traction fluid is applied to such a contact portion to efficiently transmit the driving force and to prevent direct contact between the rigid bodies. Namely, such a traction fluid exhibits an increased viscosity upon being pressed by the rigid bodies to efficiently transfer the drive force with minimum slip but shows suitable fluidity immediately upon being released from the contract portion.

One of the important characteristics of traction a fluid is the coefficient of traction. The higher the traction coefficient, the better becomes the transfer of drive force. With a traction fluid with a high traction coefficient, the traction drive device can be made compact. Another desirable property of a traction fluid is its viscosity. Too high a viscosity causes a loss of energy for the stirring of the fluid and is disadvantageous because the fluid fails to exhibit the required characteristics at the start of the operation in which the fluid is still cold. When the viscosity is considerably low, a liquid film fails to be formed between the contact portion of the rolling members at a high temperature, causing seizure.

OBJECTS OF THE INVENTION

It is therefore a general object of the present invention to provide an improved process for upgrading lower oligomers of isobutylene or of a mixture of isobutylene and a minor amount of n-butenes to higher oligomers thereof.

More particularly, it is an object of the present invention to provide an improved process for upgrading the lower oligomers of isobutylene or of a mixture of isobutylene and a minor amount of n-butenes in light polymer gasoline that is coproduced in the manufacture of polyisobutylene.

It is a related object of the present invention to provide a mixture of higher oligomers of isobutylene or of a mixture of isobutylene and a minor amount of n-butenes in which mixture the combined concentration therein of higher oligomers is at least 60 weight percent.

It is another object of the present invention to provide an improved traction fluid from the higher oligomers produced by upgrading the lower oligomers of isobutylene or of a mixture of isobutylene and a minor amount of n-butenes.

Other objects and advantages will become apparent upon reading the following detailed description and appended claims.

SUMMARY OF THE INVENTION

These objects are achieved by the process of the present invention for converting lower oligomers of isobutylene or of a mixture of isobutylene and a minor amount of n-butenes in a feedstock containing less than about 45 weight percent of higher oligomers thereof, comprising: (a) fractionating a mixture of one part by weight of the aforesaid feedstock and from about 1 to about 30 parts by weight of the oligomerization product recycled in step (c), to thereby separate the aforesaid lower oligomers from a fraction comprising the aforesaid higher oligomers; (b) oligomerizing to a predetermined extent the aforesaid lower oligomers separated in step (a) under conditions such that an oligomerization product mixture is formed comprising higher oligomers and unreacted lower oligomers; and (c) recycling the oligomerization product mixture from step (b) to step (a); and (d) recovering the higher oligomer fraction separated in step (a); wherein the fractionation and oligomerization are performed under predetermined conditions such that the higher oligomer fraction recovered in step (d) comprises a combined concentration of less than about 20 weight percent of lower oligomers, at least about 60 weight percent of higher oligomers, a weight ratio of pentamers to dimers of at least about 50, a weight ratio of tetramers to dimers of at least about 60 and less than about 20 weight percent of heptamers and above.

The present invention is also the higher oligomer fraction recovered in aforesaid step (d). In another embodiment, the present invention is the composition comprising oligomers of isobutylene and optionally n-butenes having the following distribution: a combined concentration of less than 20 weight percent of lower oligomers, a concentration of higher oligomers of at least about 60 weight percent, a weight ratio of pentamers to dimers of at least about 50, a weight ratio of tetramers to dimers of at least about 60, and less than about 20 weight percent of heptamers and above. The present invention is also a traction fluid or a fluid for continuously variable transmissions comprising at least a hydrogenated or nonhydrogenated portion of the aforesaid composition or higher oligomer fraction recovered in aforesaid step (d) as at least a portion of the base oil.

BRIEF DESCRIPTION OF THE DRAWINGS

For a more complete understanding of this invention, reference should be made to the embodiment and comparison illustrated in the accompanying drawings and described below by way of examples of the invention. In the drawings.

DETAILED DESCRIPTION OF THE PREFERRED EMBODIMENTS

Figure 1:
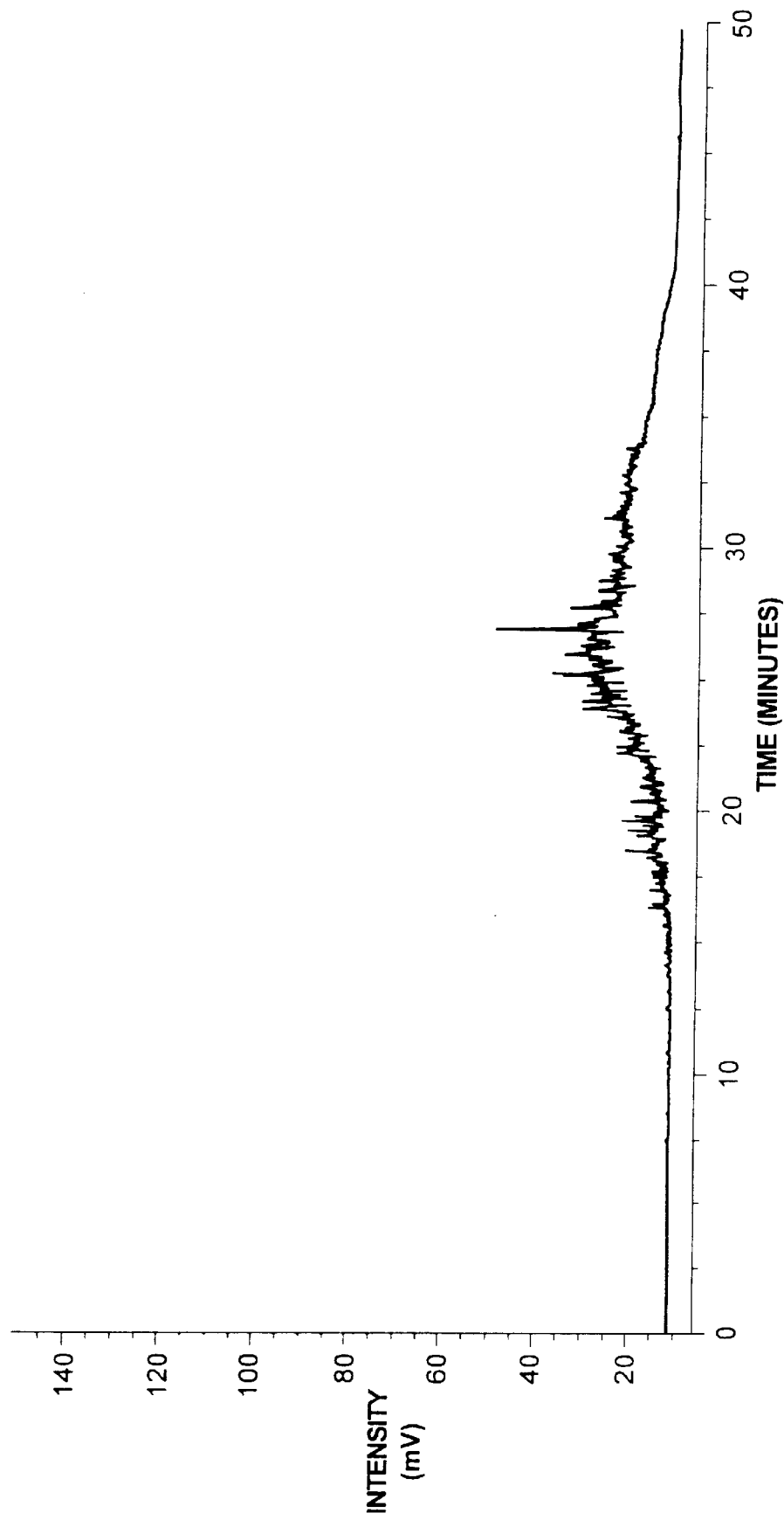
FIG. 1 is a capillary gas chromatogram of the upgraded light polymer gasoline recovered in step (d) as the product of the method of this invention.

Feedstocks that are suitable for use in the method of the present invention are mixtures of lower oligomers and higher oligomers of isobutylene or optionally oligomers of a mixture of isobutylene and a minor amount of n-butenes, which mixtures contain less than about 45 weight percent of such higher oligomers, preferably less than 35 weight percent of such higher oligomers. In this context, a minor amount of n-butenes means less than about 20, preferably less than about 15, weight percent of the aforesaid mixture. Typically, the lower oligomers being upgraded are monomers, dimers and trimers and are upgraded to tetramers and other higher oligomers. In that case, tetramers and above are considered to be the higher oligomers. However, in some other cases, the lower oligomers being upgraded also include tetramers, and in those cases, the lower oligomers are upgraded to pentamers and other higher oligomers. In those cases, pentamers and above are considered to be the higher oligomers. Preferably, the lower oligomers are monomers, dimers and trimers, and the higher oligomers are tetramers and above. Typical feedstocks comprise up to about 10 weight percent of monomers, from about 10 to about 30 weight percent of dimers, from about 30 to about 50 weight percent of trimers and less than a total of about 45, preferably less than a total of about 40, weight percent of tetramers, pentamers and other higher oligomers.

The method of the present invention is useful in conjunction with any other method which produces the aforesaid feedstock either as a desired product or a co-product. Thus, the method of the present invention is especially useful in conjunction with any conventional method for the production of a polyisobutylene having a molecular weight of at least about 300 from a stream comprising isobutylene and optionally n-butenes because any such method results in the coproduction with polyisobutylene of a lower molecular weight mixture comprising lower oligomers and higher oligomers of isobutylene and, if present, n-butenes, which mixture contains less than about 45 weight percent of such higher oligomers. Such mixtures are generally referred to as light polymer gasoline and are generally made up primarily of dimers, trimers and tetramers of the monomer(s) employed in the manufacture of polyisobutylene. Typically, such light polymer gasolines contain from about 10 to about 30 weight percent of dimers, from about 30 to about 50 weight percent of trimers, from about 20 to about 40 weight percent of tetramers and up to about 10 weight percent as the combined concentration of unreacted monomers and pentamers. The oligomeric distribution of one typical light polymer gasoline is indicated in Table 1 below. Any method of manufacturing polyisobutylene from isobutylene and optionally a mixture of isobutylene and a minor amount of n-butenes as the monomer(s) can be employed, regardless of the specific combination of aforesaid monomers, catalyst system or conditions that are employed in the production of the polyisobutylene. Any convenient separation technique can be employed to effect the separation of the aforesaid light polymer gasoline from the polyisobutylene. Typically, distillation or stripping is employed.

The first step (step (a)) of the method of the present invention is the fractionation of a mixture of one part by weight of the aforesaid feedstock, for example, the light polymer gasoline, and of from about 1 to about 30, preferably to about 10, parts by weight of the oligomerization product recycled in subsequent step (c) from a subsequent oligomerization step (step (b)) to thereby separate the aforesaid lower oligomers from the aforesaid higher oligomers. Any convenient, conventional separation technique and equipment such as distillation or stripping that are effective in making this separation can be employed. For example, when the stripper employed as the fractionator is operated at approximately atmospheric pressure and at a reboiler temperature of approximately 250° C., the higher oligomer fraction recovered from the fractionator (the stripper) in step (d) of the method of this invention contains the tetramers of isobutylene. In this case, the tetramers are considered to be higher oligomers and are not passed from the fractionator to the oligomerization reactor for further oligomerization. By contrast, when the stripper is operated at about 10 inches of mercury vacuum and at the same reboiler temperature of about 250° C., the tetramers are not included in the higher oligomer fraction that is recovered from the fractionator in step (d). In this case, the tetramers are considered to be lower oligomers and are passed from the fractionator to the oligomerization reactor for further oligomerization.

The second step (step (b)) of the method of the present invention involves the controlled oligomerization to a predetermined extent of the resulting separated lower oligomers in the presence of a solid oligomerization catalyst in any configuration permitting rapid separation of the product mixture from the catalyst, for example, in a packed bed, stirred tank or ebullated bed. The products formed include higher oligomers, and the resulting product mixture contains such higher oligomers in admixture with remaining unreacted lower oligomers. The extent of the oligomerization is controlled in part through the use of a solid oligomerization catalyst which permits quick and efficient separation of the reaction product mixture from the oligomerization catalyst before competing side or back reactions take place to a significant extent. Thereby the length of the reaction time can be controlled by allowing the reaction/product mixture to be in contact with the oligomerization catalyst only for the desired period of time and immediately thereafter quickly removing the reaction/product mixture from contact with the oligomerization catalyst to thereby terminate the reaction.

Any convenient conventional heterogenous oligomerization catalyst can be employed as the oligomerization catalyst in the oligomerization step of the method of this invention. Suitable catalysts include sulfonic acid ion exchange resins such as Amberlyst 15 or Amberlyst 35, as well as other supported sulfonic acid resins and the Nafion family of catalysts such as Nafion SAC 15 or Nafion SAS 25. Other acidic catalysts will function in this invention such as supported zeolites, or supported clay catalysts such as Y zeolites or mordenite. Preferably, the oligomerization catalyst employed is a polymer supported sulfonic acid such as a cation exchanger which contains sulfonic acid groups and which are in the H+ form. These cation exchangers exhibit a polymerization level within the general range of from 2% to 65%, and preferably from 8% to 25%, and a specific-surface area range of from 5 to 750 square meters per gram of dry catalyst material, preferably from 10 to 100 square meters per gram of dry catalyst material. Resinous materials of this type are obtained via well-established procedures, by means of the copolymerization of vinyl monomers, such as, for example, styrol or acrylic acid ester (acrylate), and divinyl polymerization agents, such as divinyl benzol. The acidic groups of the catalytic cation exchangers comprise, for example, carboxyl groups, which are generated by means of the saponification of acrylic acid ester, or sulfonic acid groups, which can be produced by means of the supplemental sulfonation of aromatic cores. In the preferred form of the present invention, a styrol-divinyl benzol polymerisate, which contains sulfonic acid groups, is employed as the oligomerization catalyst. This material can be in either gel or macroporous form, and is commercially available under a variety of trade names, such as, for example, the following: Lewatite SPC 118, SPC 108, SPC 120, SP 108, or SP 112; Amberlite 200° C.; Amberlyst; Dowex MSC-1; or Duolite C 26.

The oligomerization is performed at a temperature in the range of from about 50° C., preferably from about 80° C., more preferably from about 90° C., to about 200° C., preferably to about 160° C., more preferably to about 145° C., and at a pressure that is sufficiently high at the temperature employed as to maintain the components of the reaction/product mixture in the liquid state. Thus, the pressure is typically in the range of from about 1 pound per square inch absolute (psia), preferably from about 10 psia to about 100 psia, preferably to about 50 psia.

The length of time that the reaction product admixture is permitted to remain in contact with the solid oligomerization catalyst is set in order to achieve the desired predetermined extent of oligomerization under the reaction conditions employed. Typically, the reaction time is set such that from about 1, preferably from about 5, more preferably from about 8, to about 50, preferably to about 20, more preferably to about 16, combined mole percent of the lower oligomers in the feedstream to the oligomerization reactor are oligomerized per pass through the oligomerization reactor. In order to achieve this, the weight hourly space velocity is in the range of from about 0.1, preferably from about 1 to about 20, preferably to about 10, parts of the feed to step (b) per part of the catalyst bed by weight.

In the third step (step (c)) of the method of this invention, the entire resulting oligomerization product is recycled to the fractionation step (step (a)) where as described hereinabove a mixture of the oligomerization product and the feedstock are fractionated to thereby separate the aforesaid lower oligomers from a fraction of the aforesaid higher oligomers. In the fourth step (step (d)), this higher oligomer fraction is recovered from the fractionator as the product of the process of the present invention. When light polymer gasoline is employed as the feedstock in the method of the present invention, the product recovered in step (d) of the method of this invention is referred to herein as upgraded light polymer gasoline.

The fractionation in the first step and the oligomerization in the second step are performed under predetermined conditions such that the higher oligomer fraction recovered in the fourth step as the product mixture of the method of the present invention comprises at least about 60, preferably at least about 65, more preferably at least about 80 weight percent of the higher oligomers, and less than about 20, preferably less than about 10, more preferably less than about 5, weight percent of heptamers and oligomers higher than heptamers. Furthermore, regardless of whether (1) the tetramers are considered to be higher oligomers and are contained in the higher oligomer fraction recovered in the fourth step as a component of the product, or (2) the tetramers are considered to be lower oligomers and are oligomerized in step (b) to form higher oligomers, the weight ratio of pentamers to dimers in the higher oligomer fraction recovered as the product in the fourth step is at least about 50, preferably at least about 60, more preferably at least about 100, and the weight ratio of tetramers to dimer therein is at least about 60, preferably at least about 75, more preferably at least about 100.

The upgraded light polymer gasoline recovered in the fourth step as the product of the method of this invention and as the product of this invention has an NMR spectrum having the following characteristics:

| C-center | ppm range | likely structure | Upgraded LPG |
|---|---|---|---|
| 1 | 60.6–57.7 | RMe$_2$—CH$_2$—CMe$_2$R | 0.07 |
| 2 | 57.7–38.9 | | 17.17 |
| 3 | 38.9–36.8 | RCH$_2$—CMe$_2$—CH$_2$R | 4.27 |
| 4 | 36.8–31.8 | | 17.61 |
| 5 | 31.8–30.8 | RCH$_2$—CMe$_2$—CH$_2$ | 2.76 |
| 6 | 30.8–28.3 | RCH$_2$—CH$_2$—CH$_2$—CH$_2$CH$_2$R | 10.44 |
| 7 | 28.3–26.5 | | 10.36 |
| 8 | 26.5–19.0 | | 19.34 |
| 9 | 19.0–16.0 | RCH$_2$—CHMe—CH$_2$R | 5.43 |
| 10 | 16.0–13.0 | RCH$_2$—CH$_2$—Me | 6.08 |
| 11 | 13.0–9.8 | R$_2$CH—CH$_2$—Me | 4.21 |
| 12 | 9.8–6.8 | R$_3$C—CH$_2$—Me | 2.26 |
| Total | 60.6–6.8 | | 100.00 |

The NMR spectra hereinabove is presented as broken into 12 regions, commonly known as "carbon centers". The boundaries between regions are chosen partly on spectroscopic grounds to coincide with gaps between peaks in the spectrum and partly on structural grounds to coincide with assignments to classes of likely structural units. The carbon center 1 for upgraded light polymer gasoline indicates that the product of the method of this invention has a high degree of branching.

Figure 2:
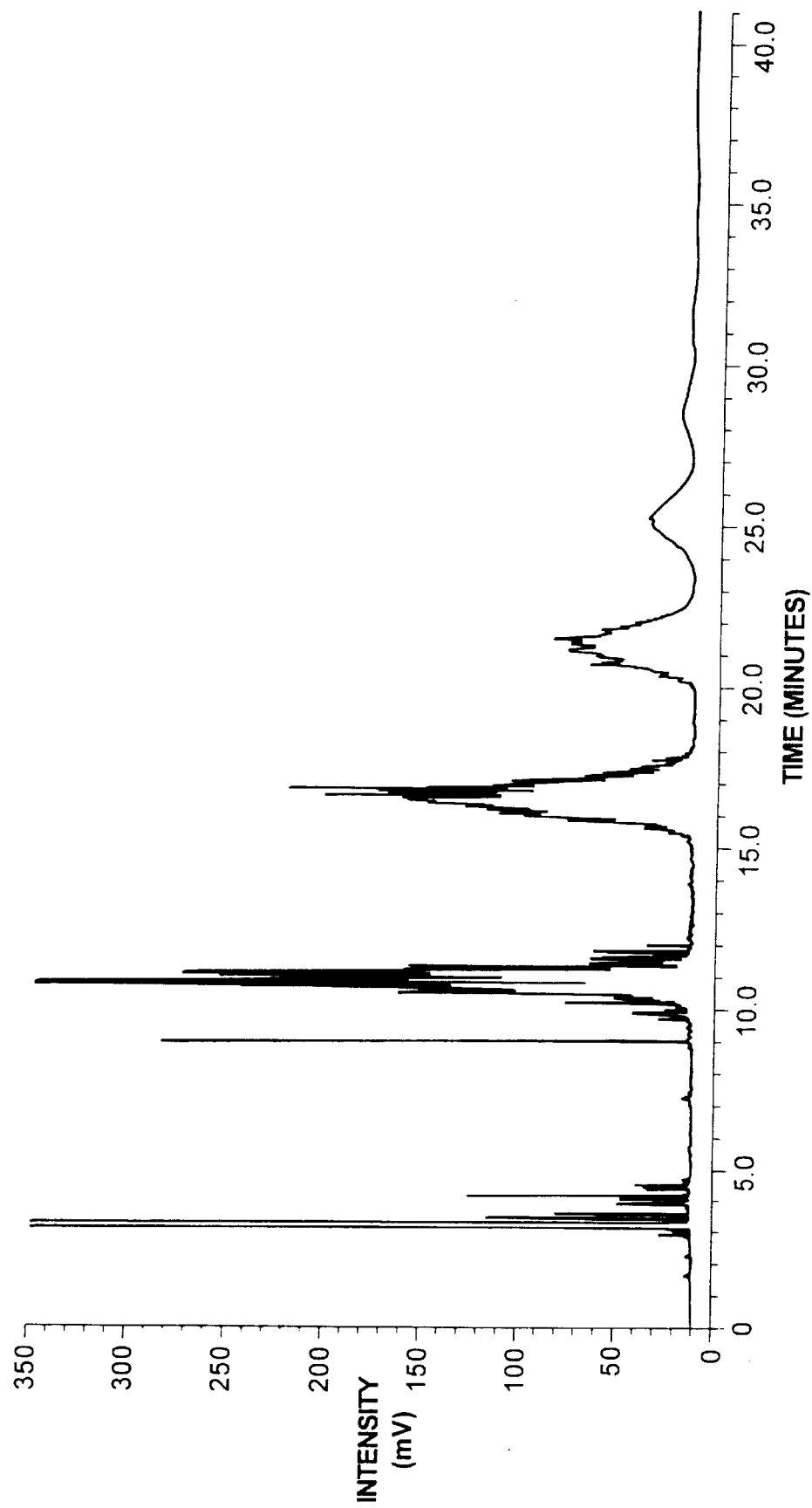
FIG. 2 is a capillary gas chromatogram of the product obtained by following the procedure of Example 15 of WO 93/02993.
Figure 3:
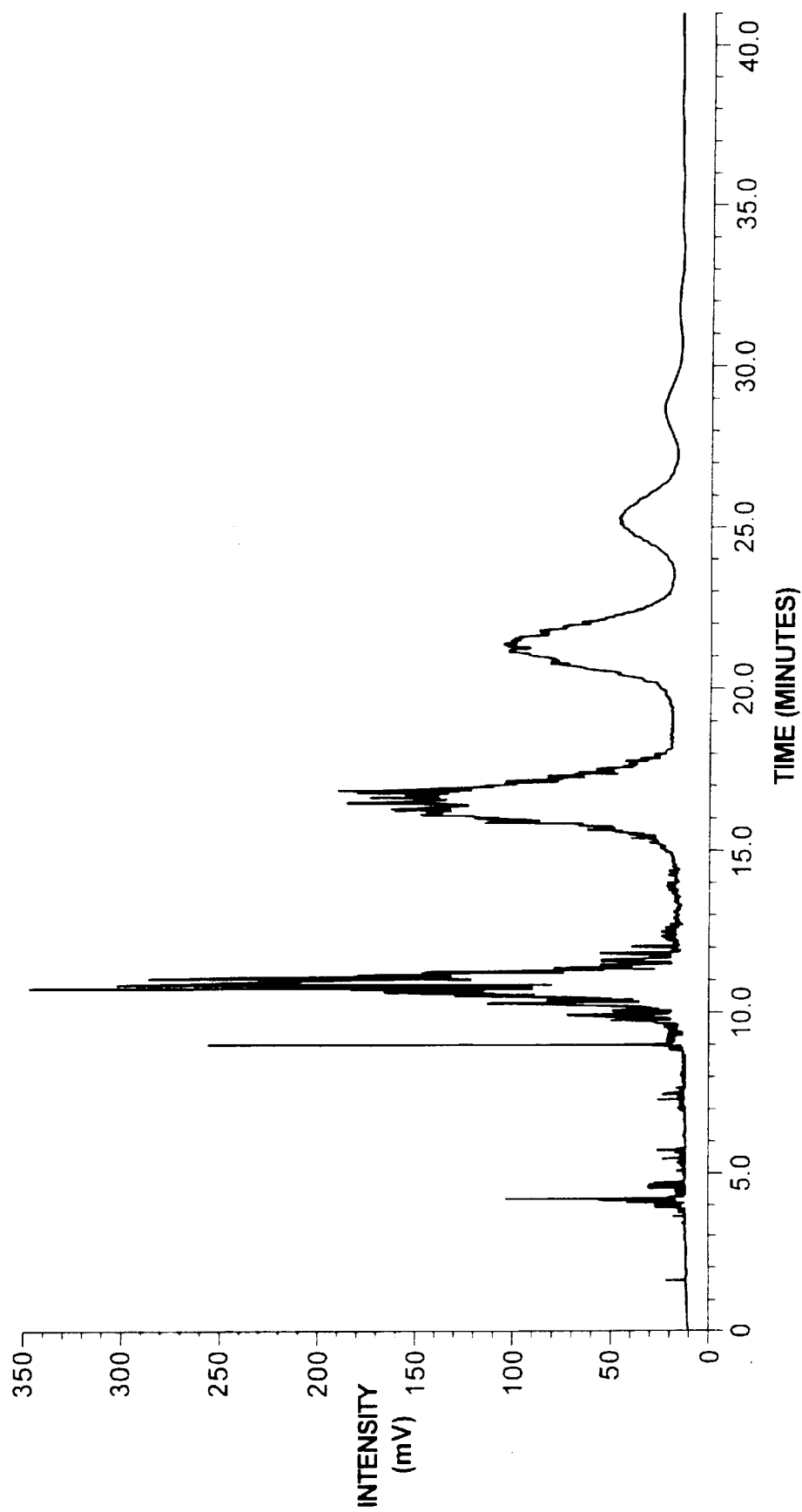
FIG. 3 is a capillary gas chromatogram of the product obtained by following the procedure of Example 19 of WO 94/15895.

FIG. 1 shows the capillary gas chromatogram of the upgraded light polymer gasoline recovered in step (d) as the product of the method of this invention and having the oligomeric distribution shown in Table 1 below. From the gas chromatogram in FIG. 1 it is apparent that the product of the method of this invention is highly isomerized. FIG. 2 shows the capillary gas chromatogram of the product obtained by following the procedure of Example 15 of WO 93/02993 discussed above. FIG. 3 shows the capillary gas chromatogram of the product obtained by following the procedure of Example 19 of WO 94/15895 discussed above. Comparison of the gas chromatograms presented in FIGS. 1, 2 and 3 illustrates that the upgraded light gasoline polymer product of the method of this invention is substantially more highly isomerized than the products of the aforesaid Examples 15 and 19.

In another preferred embodiment, a broader range of higher oligomers is produced by introducing from an external source at least one olefin, preferably a vinyl olefin or a diene containing 4 to 30 carbon atoms along with the aforesaid lower oligomers into the oligomerization reactor in step (b). The addition to the feed of step (b) of an aforesaid vinyl olefin or diene other than that present in the feedstock permits further control of the make-up of the feed to step (b), and an even wider range of customer specific oligomer oils to be produced. It also allows for production of an oligomer fraction which could not easily be made by other means. For example, co-oligomerizing the lower oligomers from step (a) with an aforesaid vinyl olefin or diene can result in the production of a higher viscosity product by the method of this invention not easily produced otherwise. For example, the viscosity of such a product can be varied by changing the amount and type of an aforesaid olefin or diene added from an external source to the feed to step (b). A range of mole percents of an aforesaid vinyl olefin or diene added from an external source in the feed to step (b) can also be varied. Generally, the identity and relative amounts of an aforesaid vinyl olefin or diene added from an external source in step (b) can be varied to control the types and relative amounts of products formed in step (b). The mole ratio of an aforesaid vinyl olefin or diene added from an external source to the lower oligomers in step (b) is typically in the range of from about 0.01, preferably from about 0.05, to about 0.5, preferably to about 0.1.

Suitable olefins and dienes for use as additional compounds to be added from an external source to the feed to step (b) in the process of the present invention contain from 4 to about 30 carbon atoms, and, preferably from about 4 to 20 carbon atoms, including mixtures thereof. Non-limiting examples of vinyl olefins include 1-butene, 1-pentene, 1-hexene, 1-heptene, 1-octene, 1-decene, 1-dodecene, 1-tetradecene, 1-hexadecene, 1-octadecene, 1-eicosene and the like. Non-limiting examples of dienes include 1,3-butadiene, 1,3 or 1,4-pentadiene, the hexadienes and higher dienes including cyclic analogs such as vinylcyclohexene. Pure olefins or dienes or a mixture of olefins or dienes can be used.

From the oligomerization reactor, the entire oligomerization product mixture is combined with the aforesaid feedstock for fractionation in step (a), with the oligomerization product and aforesaid feedstock being combined in a weight ratio of from about 30:1 to about 1:1.

The term "traction coefficient" as used herein is defined as the ratio of (a) the tractional force which is caused by slipping at the contact points between rotators which are in contact with each other in a power transmission of the rolling fraction type to (b) the normal load. The higher oligomer fraction recovered as product of the method of this invention in step (d), or at least a portion or preferably a hydrogenated portion thereof, has an excellent traction coefficient and viscosity and therefore is particularly suitable for use as a traction fluid or as all or at least a portion of the base oil in a traction fluid, such as a continuously variable transmission fluid. The higher oligomer fraction or portion thereof can be mixed with other lubricants such as mineral or synthetic oils, and various additives can be added, such as VI-improvers, pour point depressants, dispersants, detergents, anti-oxidants and the like.

A cut, which preferably is hydrogenated, of the total upgraded light polymer gasoline, comprising at least 99 weight percent of pentamers and higher oligomers and at least 40 weight percent of hexamers and higher oligomers is particularly effective as or in a traction fluid. Such cuts have viscosities at 40° C. in the range of from about 15 cSt, preferably from about 17 cSt, to about 30 cSt, preferably to about 25 cSt. Traction coefficients of specific distillation cuts of the total higher oligomer fraction recovered in step (d) of the method of the present invention were measured using the EHL Ultra Thin Measurement system made by PCS Instruments. The particular samples tested were distillation cuts taken from distillation at 185–205° C. of the aforesaid total higher oligomer fraction recovered from step (d). Data were generated under the following conditions: pressure of 0.94 to 2.5 GPa, temperatures of 0° C., 40° C., 80° C., 120° C. and 150° C., speeds of 0.2, 0.6, 1.0, 2.0 and 4.0 meters per second and side/roll ratios of 0 to 20%. The test results indicate that the samples tested are suitable traction fluids or components of traction fluids and are presented in Example 3 below.

The following examples serve to illustrate certain specific embodiments of the invention disclosed herein. These examples are for illustrative purposes only and should not be construed as limiting the scope of the invention disclosed herein, as there are many alternative modifications and variations which will be apparent to those skilled in the art and which fall within the scope and spirit of the disclosed invention.

EXAMPLE 1

One part by weight of light polymer gasoline produced as a byproduct in the commercial manufacture of polyisobutylene having a molecular weight in excess of 300 from a stream comprising predominanatly isobutylene and minor amounts of n-butenes was fed as the feedstock along with 9 parts by weight of an oligomerization product recycled from a subsequent oligomerization step to a fractionator where the light polymer gasoline and oligomerization product were fractionated to form one fraction comprising monomers, dimers and trimers and a second fraction comprising tetramers and other higher oligomers which was recovered as the product and referred to as upgraded light polymer gasoline. The lower oligomers were monomers, dimers and trimers, and the higher oligomers were tetramers and above. The second fraction was approximately 90 weight percent of the total amount of the combination of light polymer gasoline and oligomerization product fed to the fractionator and was recycled to the aforesaid oligomerization reactor for additional oligomerization. This process was performed on a continuous basis for 15 days. The fractionator was a distillation column operated at a bottoms temperature of about 250° C. and a pressure of about 0 pounds per square inch gauge. The oligomerization was performed using a solid Amberlyst 15 catalyst in a packed bed at a weight hourly space velocity of 4.85 at a reaction temperature of about 100° C. and at a reaction pressure of about 0 pounds per square inch gauge.

Samples of upgraded light polymer gasoline recovered as product were fractionated by distillation to form three fractions having different viscosities of 4 cSt, 19 cSt and 28 cSt at 38° C. The $C_4$ oligomer distributions of each of the light polymer gasoline feedstock, unfractionated upgraded light polymer gasoline and the 4 cSt, 19 cSt and 28 cSt fractions thereof were obtained by capillary gas chromatography measurement and are reported in Table 1.

TABLE 1

| | C4 Oligomer Distribution | | | | |
|---|---|---|---|---|---|
| | Light Polymer Gasoline Feedstock | Upgraded Light Polymer Gasoline Product | Fractions of Upgraded Light Polymer Gasoline Product | | |
| | | | 4 cSt | 19 cSt | 28 cSt |
| monomers | 3.81 | <0.01 | <0.01 | <0.01 | <0.01 |
| dimers | 19.1 | 0.115 | <0.01 | <0.01 | <0.01 |
| trimers | 40.6 | 8.81 | 0.036 | 0.212 | <0.01 |
| tetramers | 31.8 | 51.3 | 82.8 | 0.105 | <0.01 |
| pentamers | 4.66 | 31.8 | 17.1 | 55.4 | 18.4 |
| hexamers | 0.010 | 7.93 | 0.058 | 35.5 | 64.9 |
| heptamers+ | +0.010 | 0.051 | <0.01 | 8.74 | 16.6 |

After being hydrogenated, the 19 cSt fraction was measured to have a Brookfield viscosity at −40° C. of 37,100 cps, kinematic viscosities at 40° C. and 100° C. of 16.7 and 3.3 cSt, respectively, a Cleveland Open Cup (COC) flash point of 162° C., a pour point of less than −65° C., and a traction coefficient of 0.087 measured at 40° C., 0.94 GPa pressure, a speed of 4 meters per second, and a slide/roll ratio of 3%, indicating that this fraction of the upgraded light polymer gasoline has a combination of properties, especially traction coefficient and viscosity, that render it especially suitable for use as a base oil for traction fluids, such as a continuously variable transmission fluid.

EXAMPLE 2

The light polymer gasoline feedstock (1,221 gm) having the oligomer distribution substantially as shown in Table 1 was produced as a byproduct in a commercial polybutene plant and was charged to a batch vacuum stripper operated at 20 inches Hg vacuum. This stripper consisted of a one liter boot, 24 inch long by 2 inch diameter column packed with stainless steel mesh, and a one liter overhead vessel. With this stripper and under these conditions, light polymer gasoline and oligomerization product were fractionated to form a fraction comprising pentamers and other higher oligomers which was recovered as the higher oligomer product and referred to as upgraded light polymer gasoline and a second fraction comprising monomers, dimers, trimers, and tetramers. The lower oligomers were monomers, dimers, trimers, and tetramers, and the higher oligomers were pentamers and above. The lower oligomer fraction was fed to an oligomerization reactor for additional oligomerization. This oligomerization reactor consisted of a packed bed of solid catalyst weighing 280 grams. The product from the aforesaid oligomerization reactor was continuously recycled to the aforesaid vacuum stripper and fractionated into the aforesaid higher oligomer fraction and lower oligomer fraction. This process was performed on a continuous basis until the boiling temperature of the higher oligomer fraction in the stripper boot reached 250° C. at the operating pressure of 20 inches Hg vacuum. The oligomerization was performed using a solid Amberlyst 15 catalyst in a packed bed at a weight hourly space velocity of about 2.9 to about 6.3 and at a temperature of about 90° C. to about 110° C. and at a pressure of about 24 to about 32 pounds square inch gauge.

The $C_4$ oligomer distributions of each of the upgraded light polymer gasoline were obtained by capillary gas chromatography measurement and are reported in Table 2.

TABLE 2

| C4 Oligomer Distribution of Upgraded Light Polymer Gasoline Product | |
|---|---|
| monomers | <0.01 |
| dimers | 0.062 |
| trimers | 0.706 |
| tetramers | 6.54 |
| pentamers | 38.1 |
| hexamers | 40.3 |
| heptamers+ | 14.3 |

EXAMPLE 3

Five blends of different heavy fractions of upgraded light polymer gasolines were tested for their suitability as traction fluids. The light polymer gasolines were produced as a coproduct of the commercial manufacture of polyisobutylene having a molecular weight of at least 300 from a mixture of isobutylene and a minor amount of n-butenes. In each case, the light polymer gasoline feedstock had an oligomeric distribution that was substantially similar to that shown for the light polymer gasoline feedstock in Table 1 and was treated by the process of the present invention to thereby produce upgraded liquid polymer gasoline as the product of the method of the present invention. In each case, the upgraded light polymer gasoline had an oligomeric distribution substantially similar to that shown for the upgraded light polymer gasoline in Table 1 and each of ULPG-1-2-3-4 and -5 was hydrogenated over an alumina-supported nickel catalyst.

ULPG-1

The upgraded light polymer gasoline was fractionated by wiped film evaporation to recover a heavy fraction having a viscosity of about 11 cSt at 40° C. This heavy fraction was divided into six portions, each of which was distilled to remove about 35 percent by weight of the lighter components. The remaining volumes of each of the six portions were combined. The resulting combination had a viscosity of 16.7 cSt at 40° C. and is designated as ULPG-1.

ULPG-2

Fifty-five gallons of upgraded light polymer gasoline were distilled in a distillation column containing about 100 trays under vacuum to produce ten distillate cuts of approximately equal volume. The temperatures at which the distillates were collected, the volume and weight of each cut as a percent of the upgraded light polymer gasoline, the API gravity, specific gravity viscosity at 38° C., and flash point of each cut are reported in Table 3.

TABLE 3

| Cut | Temp., ° C. | API Gr. | Sp. Gr. | Yield Vol. % | Yield Wt. % | Vis. @ 38° C. | Flash Point ° C. |
|---|---|---|---|---|---|---|---|
| 1 | 202 | 50.2 | 0.7788 | 9.51 | 9.12 | 1.44 | 63 |
| 2 | 223 | 46.6 | 0.7945 | 9.77 | 9.56 | 2.07 | 88 |
| 3 | 240 | 45.3 | 0.8003 | 9.94 | 9.8 | 2.73 | 97 |
| 4 | 243 | 44.4 | 0.8044 | 9.84 | 9.75 | 3.19 | 102 |
| 5 | 252 | 43.5 | 0.8095 | 9.64 | 9.82 | 3.57 | 102 |
| 6 | 260 | 42.5 | 0.8132 | 9.91 | 9.93 | 4.20 | 104 |
| 7 | 269 | 42.1 | 0.8151 | 9.95 | 9.99 | 5.06 | 96 |
| 8 | 284 | 40.8 | 0.8212 | 9.96 | 10.1 | 7.91 | 138 |
| 9 | 299 | 39.2 | 0.8269 | 9.89 | 10.1 | 10.46 | 143 |
| 10 |  | 36.8 | 0.8408 | 10.1 | 10.56 | 37.60 | 177 |

One part by weight of cut no. 9 and one part by weight of cut no. 10 were combined to produce a fluid having a viscosity of 17.8 cSt at 40° C. The resulting product is designated as ULPG-2.

ULPG-3

One part by weight of cut no. 9 and 2 parts by weight of cut no. 10 as described above and in Table 3 were blended to produce a fluid having a viscosity of 22.9 cSt at 40° C. This fluid is designated as ULPG-3.

ULPG-4

One part by weight of cut no. 9 and 3 parts by weight of cut no. 10 as described above and in Table 3 were blended to produce a fluid having a viscosity of 22.9 cSt at 40° C. This fluid is designated as ULPG-4.

ULPG-5

The upgraded light polymer gasoline was fractionated by thin film evaporation to recover a heavy fraction having a viscosity of about 10 cSt at 40° C. This heavy fraction was divided into three portions, each of which was distilled to remove about 62 percent by weight of the lighter components. The remaining volumes of each of the three portions were combined. The resulting combination had a viscosity of 24.2 cSt at 40° C. and is designated as ULPG-5.

The viscosities, flash points and traction coefficients of ULPG-1, -2, -3, -4, and -5 were measured and are reported in Table 4. The results confirm that the product of the method of this invention or a portion thereof is highly suitable for use as a traction fluid or at least a portion of the base oil.

TABLE 4

| | Traction Data | | | | | | | |
|---|---|---|---|---|---|---|---|---|
| | Kinematic Viscosity | Kinematic Viscosity | Brookfield Viscosity | COC Flash | Traction Coefficient | | | |
| | | | | | 3% Slide/Roll Ratio | | 5% Slide/Roll Ratio | |
| Fluids | at 40° C., cSt | at 100° C., cSt | at −40° C. cps | Point, ° C. | 40° C. | 120° C. | 40° C. | 120° C. |
| ULPG-1 | 16.7 | 3.3 | 38,100 | 158 | 0.084 | 0.030 | 0.094 | 0.038 |
| ULPG-2 | 17.8 | 3.4 | 45,100 | 160 | 0.086 | 0.027 | 0.097 | 0.035 |
| ULPG-3 | 20.4 | 3.7 | 70,200 | 163 | 0.079 | 0.027 | 0.098 | 0.038 |

TABLE 4-continued

| | | | | | Traction Data | | | |
|---|---|---|---|---|---|---|---|---|
| | Kinematic | Kinematic | Brookfield | COC | Traction Coefficient | | | |
| | Viscosity | Viscosity | Viscosity | Flash | 3% Slide/Roll Ratio | | 5% Slide/Roll Ratio | |
| Fluids | at 40° C., cSt | at 100° C., cSt | at −40° C. cps | Point, ° C. | 40° C. | 120° C. | 40° C. | 120° C. |
| ULPG-4 | 22.9 | 3.9 | 95,700 | 162 | 0.089 | 0.031 | 0 098 | 0.040 |
| ULPG-5 | 24.2 | 4.0 | 117,800 | 173 | 0.088 | 0.033 | 0.097 | 0.042 |

From the above description, it is apparent that the objects of the present invention have been achieved. While only certain embodiments have been set forth, alternative embodiments and various modifications will be apparent from the above description to those skilled in the art. These and other alternatives are considered equivalents and are within the spirit and scope of the present invention.

What is claimed is:

1. A process for converting lower oligomers of isobutylene or optionally a mixture of isobutylene and a minor amount of n-butenes in a feedstock containing less than about 45 weight percent of higher oligomers thereof, comprising:
   (a) fractionating a mixture of from about one part by weight of the aforesaid feedstock and from about 1 to about 30 parts by weight of the oligomerization product recycled in step (c), to thereby separate the aforesaid lower oligomers from a fraction comprising the aforesaid higher oligomers;
   (b) oligomerizing to a predetermined extent the aforesaid lower oligomers separated in step (a) under conditions such that an oligomerization product mixture is formed comprising higher oligomers and unreacted lower oligomers;
   (c) recycling the oligomerization product mixture from step (b) to step (a); and
   (d) recovering the higher oligomer fraction separated in step (a);
wherein the fractionation and oligomerization are performed under predetermined conditions such that the higher oligomer fraction recovered in step (d) comprises less than about 20 weight percent of lower oligomers, at least about 60 weight percent of higher oligomers, a weight ratio of pentamers to dimers of at least about 50, and a weight ratio of tetramers to dimers of at least about 60 and less than about 20 weight percent of heptamers and above.

2. The process of claim 1 wherein the feedstock comprises up to about 10 weight percent of monomers, from about 10 to about 30 weight percent of dimers, from about 30 to about 50 weight percent of trimers, and less than a total of about 45 weight percent of tetramers and other higher oligomers.

3. The process of claim 1 wherein the lower oligomers are monomers, dimers and trimers of isobutylene or optionally a mixture of isobutylene and a minor amount of n-butenes.

4. The process of claim 1 wherein the lower oligomers are monomers, dimers, trimers and tetramers of isobutylene or optionally a mixture of isobutylene and a minor amount of n-butenes.

5. The process of claim 1 wherein the mixture being fractionated in step (a) comprises from about 1 to about 30 parts of the oligomerization product recycled in step (c) per part of the feedstock by weight.

6. The process of claim 1 wherein the oligomerization in step (b) is performed in the presence of a solid oligomerization catalyst.

7. The process of claim 1 wherein the oligomerization in step (b) is performed at a temperature in the range of from about 50° C. to about 200° C.

8. The process of claim 1 wherein the fractionation and oligomerization are performed under conditions such that the higher oligomer fraction recovered in step (d) comprises a combined concentration of higher oligomers of at least 65 weight percent, a weight ratio of pentamers to dimers of at least about 60 and a weight ratio of tetramers to dimers of at least about 75.

9. The process of claim 1 wherein at least one diene or vinyl olefin containing from 4 to 30 carbon atoms is added from an external source and is oligomerized in step (b) with the aforesaid lower oligomers.

10. The process of claim 9 wherein the mole ratio of the at least one diene or vinyl olefin added from an external source to the lower oligomers in step (b) is in the range of from about 0.01 to about 0.5.

11. The process of claim 1 wherein the feedstock is coproduced in the manufacture of polyisobutylene having a molecular weight of at least about 300 from isobutylene or optionally a mixture of isobutylene and a minor amount of n-butenes, and is separated from polyisobutylene prior to step (a).

12. The higher oligomer fraction recovered in step (d) of the process of claim 1.

13. The higher oligomer fraction product recovered in step (d) of the process of claim 9.

14. The higher oligomer fraction product recovered in step (d) of the process of claim 11.

15. A composition comprising oligomers of isobutylene or optionally oligomers of a mixture of isobutylene and a minor amount of n-butenes having the following distribution: a concentration of less than 20 weight percent of monomers, dimers and trimers, a concentration of at least about 60 weight percent of higher oligomers, a weight ratio of pentamers to dimers of at least about 50 and a weight ratio of tetramers to dimers of at least about 60 and less than 20 weight percent of heptamers and above.

16. The composition of claim 15 wherein the weight ratio of pentamers to dimers is at least about 60.

17. The composition of claim 15 wherein the weight ratio of tetramers to dimers is at least about 75.

18. A traction fluid comprising at least a portion of the higher oligomer fraction recovered in step (d) of the process of claim 1 as at least a portion of the base oil.

19. A traction fluid comprising at least a portion of the product recovered in step (d) of the process of claim 11 as at least a portion of the base oil.

20. A traction fluid comprising at least a portion of the composition of claim 15 as at least a portion of the base oil.

* * * * *

UNITED STATES PATENT AND TRADEMARK OFFICE
CERTIFICATE OF CORRECTION

PATENT NO. : 6,239,321 B1  Page 1 of 1
DATED : May 29, 2001
INVENTOR(S) : Allen B. Mossman, Egils Vitands It is certified that error appears in the above-identified patent and that said Letters Patent is hereby corrected as shown below:

Column 12,
Line 29, "a viscosity of 22.9 at" should read -- a viscosity of 20.4 at --

Column 13,
Line 10, "0.031    0 098    0.040" should read -- 0.031    0.098    0.040 --

Signed and Sealed this

Fifteenth Day of January, 2002

Attest:

JAMES E. ROGAN
Attesting Officer        Director of the United States Patent and Trademark Office